US009862765B2

(12) United States Patent
Zhang et al.

(10) Patent No.: US 9,862,765 B2
(45) Date of Patent: Jan. 9, 2018

(54) IL-17A BINDING AGENT AND USES THEREOF

(71) Applicants:Shanghai Hengrui Pharmaceutical Co., Ltd., Shanghai (CN); Jiangsu Hengrui Medicine Co., Ltd., Lianyungang, Jiangsu (CN)

(72) Inventors: Lianshan Zhang, Shanghai (CN); Jiajian Liu, Shanghai (CN); Guoqing Cao, Shanghai (CN); Piaoyang Sun, Jiangsu (CN)

(73) Assignees: Shanghai Hengrui Pharmaceutical Co., Ltd., Shanghai (CN); Jiangsu Hengrui Medicine Co., Ltd., Lianyungan, Jiangsu (CN)

( * ) Notice: Subject to any disclaimer, the term of this patent is extended or adjusted under 35 U.S.C. 154(b) by 0 days.

(21) Appl. No.: 15/035,550

(22) PCT Filed: Oct. 27, 2014

(86) PCT No.: PCT/CN2014/089542
§ 371 (c)(1),
(2) Date: May 10, 2016

(87) PCT Pub. No.: WO2015/070697
PCT Pub. Date: May 21, 2015

(65) Prior Publication Data
US 2016/0289321 A1 Oct. 6, 2016

(30) Foreign Application Priority Data
Nov. 18, 2013 (CN) .......................... 2013 1 0580942

(51) Int. Cl.
| A61K 39/395 | (2006.01) |
| C12N 15/63 | (2006.01) |
| C07K 16/24 | (2006.01) |
| C07K 14/54 | (2006.01) |
| A61K 39/00 | (2006.01) |

(52) U.S. Cl.
CPC ............ *C07K 16/244* (2013.01); *C07K 14/54* (2013.01); *C07K 16/248* (2013.01); *A61K 2039/505* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/567* (2013.01); *C07K 2317/76* (2013.01); *C07K 2317/92* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| 6,309,636 B1 * | 10/2001 | do Couto ........... A61K 51/1051 424/133.1 |
| 8,110,191 B2 | 2/2012 | Allan et al. |
| 8,193,319 B2 | 6/2012 | Presta et al. |
| 2010/0266531 A1 * | 10/2010 | Hsieh ................... C07K 16/241 424/85.2 |
| 2015/0152178 A1 | 6/2015 | Di Padova et al. |

FOREIGN PATENT DOCUMENTS

| CN | 101001645 A | 7/2007 |
| CN | 101326195 A | 12/2008 |
| CN | 101646690 A | 2/2010 |
| WO | 2010034443 A1 | 4/2010 |

OTHER PUBLICATIONS

International Search Report dated Jan. 30, 2015 in International Application No. PCT/CN2014/089542.
Aggarwal et al., "IL-17: prototype member of an emerging cytokine family," Journal of Leukocyte Biology, vol. 71, pp. 1-8 (Jan. 2002).
Lubberts et al., "Treatment With a Neutralizing Anti-Murine Interleukin-17 Antibody After the Onset of Collagen-Induced Arthritis Reduces Joint Inflammation, Cartilage Destruction, and Bone Erosion," Arthritis & Rheumatism, vol. 50, No. 2, pp. 650-659 (Feb. 2004).
Spriggs, "Interleukin-17 and Its Receptor," Journal of Clinical Immunology, vol. 17, No. 5, pp. 366-369 (1997).
Kolls et al., "Interleukin-17 Family Members and Inflammation," Immunity, vol. 21, pp. 467-476 (Oct. 2004).
Kawaguchi et al., "IL-17 cytokine family," Journal of Allergy and Clinical Immunology, vol. 114, pp. 1265-1273 (2004).
Moseley et al., "Interleukin-17 family and IL-17 receptors," Cytokine & Growth Factor Reviews, vol. 14, pp. 155-174 (2003).
GenBank Accession No. AAO59842 [retrieved from Internet on May 9, 2016]. <URL: http://www.ncbi.nlm.nih.gov/protein/28875256>. (1 page).

* cited by examiner

*Primary Examiner* — Dong Jiang
(74) *Attorney, Agent, or Firm* — Panitch Schwarze Belisario & Nadel LLP

(57) ABSTRACT

Provided is an antibody capable of specially recognizing IL-17A and binding to IL-17A. The antibody can be used for treating inflammation and autoimmune diseases caused by elevated expression of interleukin-17A, such as psoriasis, psoriatic arthritis, ankylosing spondylitis, multiple sclerosis, and inflammatory arthritis.

25 Claims, No Drawings

IL-17A BINDING AGENT AND USES THEREOF

CROSS-REFERENCE TO RELATED APPLICATION

This application is a Section 371 of International Application No. PCT/CN2014/089542, filed Oct. 27, 2014, which was published in the Chinese language on May 21, 2015, under International Publication No. WO 2015/070697 A1, and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "seqlist-revised", creation date of May 9, 2016, and having a size of 10.9 kb. The sequence listing submitted via EFS-Web is part of the specification and is herein incorporated by reference in its entirety.

FIELD OF THE INVENTION

The present invention relates to an IL-17A binding agent and its use as a therapeutic agent, in particular as a therapeutic agent for a variety of inflammatory or autoimmune diseases.

BACKGROUND

Cytokines of the interleukin-17 family are named IL-17A to IL-17F. Correspondingly, the family of their receptors, named IL-17 receptor A to IL-17 receptor E, have also been identified. The IL-17 cytokines bind to their corresponding receptors and thereby mediate different inflammatory responses.

The classical member of the family is IL-17A. Lymphocytes that migrate to infection or injury sites can secrete IL-17A. IL-17A induces the expression of inflammatory cytokines and chemokines, thereby recruiting additional immune cells to the inflammation site and exacerbating the inflammatory response. In addition, IL-17A induces the expression of some factors relevant to tissue repair, thus accelerating recovery of the organism. Although interleukin-17A has the effect of amplifying the immune defense response and protecting organisms during the process of anti-infection and tissue repair in the host, interleukin-17A is highly expressed in many patients suffering from autoimmune diseases and cancers, and excessive expression of interleukin-17A plays a negative role in pathologic development because it can induce the expression of various inflammatory factors. Many animal experiments have shown that the pathological severity of various autoimmune diseases can be effectively suppressed by interleukin-17A deficiency or interleukin-17A antibody neutralization. There is evidence that IL-17 signaling could be an effective target for treating autoimmune diseases, including rheumatoid arthritis (RA), psoriasis, Crohn's disease, multiple sclerosis (MS), psoriasis disease, asthma and lupus (see, for example, Aggarwal et al., J. Leukoc. Biol, 71 (1): 1-8 (2002); Lubberts et al.).

Human IL-17 is a gene encoding a full-length polypeptide having 155 amino acids. The polypeptide comprises a 19-amino-acid signal sequence and a 132-amino-acid mature region. With a relative molecular weight of 17,000 Da, human IL-17A is a glycoprotein existing in the form of a homodimer or a heterodimer (Spriggs et al, J. Clin. Immunol, 17: 366-369 (1997)). The IL-17F homolog can combine with IL-17A to form an IL-17A/F heterodimer. The amino acid sequence of IL-17F (IL-24, ML-1) has up to 55% similarity to that of IL-17A, and both have the same receptor, IL-17R. IL-17R is ubiquitously expressed in a variety of cells, including vascular endothelial cells, peripheral T cells, B cells, fibroblasts, myelomonocytes and bone marrow stromal cells (Kolls et al, Immunity, 21: 467-476 (2004); Kawaguchi et al, J. Allergy Clin. Immunol, 114 (6): 1267-1273 (2004); Moseley et al, Cytokine Growth Factor Rev, 14 (2): 155-174 (2003)).

From the discovery of interleukin-17A, until now, a variety of anti-IL-17A antibodies have been identified, such as CN101001645A, CN101326195A, CN101646690A, but there is still a need for the development of various kinds of improved antibodies to effectively reduce or eliminate IL-17 activity in inflammatory responses and autoimmune diseases.

SUMMARY OF THE INVENTION

The present invention provides an anti-IL-17A antibody with improved affinity and improved half-life.

The present invention provides an IL-17A binding agent, comprising:

An antibody light chain variable region, comprising 0-3 LCDR regions selected from those shown in SEQ ID NO: 13, SEQ ID NO: 14, and SEQ ID NO: 15; and An antibody heavy chain variable region, comprising 0-3 HCDR regions selected from those shown in SEQ ID NO: 10, SEQ ID NO: 11, and SEQ ID NO: 12;

wherein the numbers of CDR regions of the antibody light chain variable region and the antibody heavy chain variable region are not simultaneously 0.

According to some embodiments of the present invention, the IL-17A binding agent comprises SEQ ID NO: 13.

According to some embodiments of the present invention, the IL-17A binding agent comprises SEQ ID NO: 14.

According to some embodiments of the present invention, the IL-17A binding agent comprises SEQ ID NO: 15.

According to some embodiments of the present invention, the IL-17A binding agent comprises SEQ ID NO: 10.

According to some embodiments of the present invention, the IL-17A binding agent comprises SEQ ID NO: 11.

According to some embodiments of the present invention, the IL-17A binding agent comprises SEQ ID NO: 12.

According to some embodiments of the present invention, the IL-17A binding agent comprises one LCDR region selected from SEQ ID NO: 13, SEQ ID NO: 14 and SEQ ID NO: 15.

According to some embodiments of the present invention, the IL-17A binding agent comprises one HCDR region selected from those shown in SEQ ID NO: 10, SEQ ID NO: 11 and SEQ ID NO: 12.

According to some embodiments of the present invention, the IL-17A binding agent comprises two LCDR regions selected from those shown in SEQ ID NO: 13, SEQ ID NO: 14 and SEQ ID NO: 15.

According to some embodiments of the present invention, the IL-17A binding agent comprises two HCDR regions selected from those shown in SEQ ID NO: 10, SEQ ID NO: 11 and SEQ ID NO: 12.

According to some embodiments of the present invention, the IL-17A binding agent comprises three LCDR regions, wherein the amino acid sequence of LCDR1 is shown in SEQ ID NO: 13, the amino acid sequence of LCDR2 is shown in SEQ ID NO: 14 and the amino acid sequence of LCDR3 is shown in SEQ ID NO: 15.

According to some embodiments of the present invention, the IL-17A binding agent comprises three HCDR regions, wherein the amino acid sequence of HCDR1 is shown in SEQ ID NO: 10, the amino acid sequence of HCDR2 is shown in SEQ ID NO: 11 and the amino acid sequence of HCDR3 is shown in SEQ ID NO: 12.

According to some embodiments of the present invention, the antibody light chain variable region of the IL-17A binding agent further comprises a light chain framework (FR) region derived from murine κ or λ chain or a variant thereof. In some embodiments, the amino acid sequence of the antibody light chain variable region is SEQ ID NO: 2. In further embodiments, the IL-17A binding agent comprises a light chain constant region derived from murine κ or λ chain or a variant thereof.

According to some embodiments of the present invention, antibody heavy chain variable region of the IL-17A binding agent further comprises a heavy chain FR region derived from murine IgG1, IgG2, IgG3, IgG4 or a variant thereof. In some embodiments, the amino acid sequence of the antibody heavy chain variable region is SEQ ID NO: 1. In further embodiments, the IL-17A binding agent comprises heavy chain constant region derived from murine IgG1, IgG2, IgG3, IgG4 or a variant thereof.

According to some embodiments of the present invention, the antibody light chain variable region of the IL-17A binding agent further comprises a light chain FR region derived from human κ or λ chain or a variant thereof. In some embodiments, the light chain FR region of the antibody light chain variable region is the human germline light chain A10 FR region, whose amino acid sequence is shown in SEQ ID NO: 4, or a variant thereof. In some embodiments, the variant of the antibody light chain variable region FR region refers to a human germline light chain A10 FR region with 0-10 amino acid mutations. In some embodiments, the amino acid mutation in an FR region variant of the light chain variable region is one or more selected from the group consisting of F71Y, K49Y, Y36F, and L47W. In some embodiments, the antibody light chain is selected from SEQ ID NO: 9 and a variant thereof. In further embodiments, the IL-17A binding agent comprises light chain constant region derived from human κ or λ chain or a variant thereof.

According to some embodiments of the present invention, the antibody heavy chain variable region of the IL-17A binding agent further comprises the heavy chain FR region derived from human IgG1, IgG2, IgG3, IgG4 or a variant thereof. In some embodiments, the heavy chain FR region of the antibody heavy chain variable region is the FR region of the human germline heavy chain VH1-18, whose amino acid sequence is shown in SEQ ID NO: 3, or a variant thereof. In some embodiments, a FR region variant of the antibody heavy chain variable region refers to a human germline heavy chain VH1-18 region with 0-10 amino acid mutations. In some embodiments, the amino acid mutation in an FR region variant of the heavy chain variable region is one or more selected from the group consisting of: A93T, T71A, M48I, V67A, M69L, T73D, and S76N; In some embodiments, the antibody heavy chain is selected from SEQ ID NO: 5, SEQ ID NO: 6, SEQ ID NO: 7 and SEQ ID NO: 8. In further embodiments, the IL-17A binding agent comprises heavy chain constant region derived from human IgG1, IgG2, IgG3, IgG4 or a variant thereof.

Furthermore, according to some embodiments of the present invention, provided is a vector expressing an IL-17A binding agent described above. The host cells express and secrete the IL-17A binding agent after being transfected with the vector.

According to some embodiments of the present invention, the vector comprises a nucleotide encoding the IL-17A binding agent of the present invention.

Furthermore, according to some embodiments of the present invention, provided is a pharmaceutical composition that comprises the IL-17A binding agent as described above and a pharmaceutically acceptable excipient, diluent or carrier.

Furthermore, according to some embodiments, the present invention also provides a use of the described IL-17A binding agent, or of the pharmaceutical composition containing the same, in the preparation of a medicament for the treatment of IL-17-mediated diseases or disorders. The diseases comprise inflammatory or autoimmune diseases and are selected from the group consisting of psoriasis, psoriatic arthritis, ankylosing spondylitis, multiple sclerosis, and inflammatory arthritis. The inflammatory disease is preferably inflammatory arthritis. The inflammatory arthritis is selected from the group consisting of osteoarthritis, rheumatoid arthritis, rheumatic arthritis and osteoporosis, and is preferably rheumatic arthritis.

According to some embodiments, the present invention also provides the use of the described IL-17A antibody, or a pharmaceutical composition comprising the same, in the preparation of a medicament for the treatment of IL-17-mediated diseases or disorders. The diseases comprise inflammatory or autoimmune diseases. The inflammatory disease is preferably inflammatory arthritis. The inflammatory arthritis is selected from the group consisting of osteoarthritis, rheumatoid arthritis and osteoporosis.

According to some embodiments, the present invention also provides a method for treating a disease or disorder mediated by IL-17, the method comprising administering to a subject in need thereof a therapeutically effective amount of an IL-17A binding agent as described above, or of a humanized IL-17A antibody or a pharmaceutical composition containing the same.

So that the invention can be more readily understood, certain technical and scientific terms are specifically defined below. Unless specifically defined elsewhere in this document, all other technical and scientific terms used herein have the meaning commonly understood by one of ordinary skill in the art to which this invention belongs.

I. Terms

As used herein, the single-letter code and the three-letter code for amino acids are as described in J. Biol. Chem, 243, (1968) p 3558.

As used herein, "binding agent" refers to a soluble receptor or fragments or analogs thereof, or to antibodies or fragments or analogs thereof that are capable of binding to the target. "IL-17A binding agent," according to the present invention, refers to an antibody or fragment or analog thereof that is capable of specifically recognizing and binding to IL-17A.

The term "IL-17A" generally refers to a natural or recombinant human IL-17A, and to non-human homologues of human IL-17A. Unless otherwise indicated, the molecular weight of an IL-17A homodimer is used (for example, 30 KDa for human IL-17A) to calculate the molar concentration of IL-17A.

As used herein, "Antibody" refers to immunoglobulin, a four-peptide chain structure consisting of two identical heavy chains and two identical light chains connected via a disulfide bond. Immunoglobulin heavy chain constant regions exhibit different amino acid components and orders, and therefore present different antigenicity. Accordingly, immunoglobulins can be divided into five categories, called immunoglobulin isotypes, namely IgM, IgD, IgG IgA and IgE. According to the amino acid components of the hinge region and the number and location of heavy chain disulfide bonds, Ig's in the same category can further be divided into different sub-types, for example, IgG can be divided into IgG1, IgG2, IgG3 and IgG4. Light chains can be divided into κ or λ chains by different constant regions.

The regions of about 110 amino acids near the N-termini of the antibody heavy and light chains vary widely and are known as the variable regions (V regions); the remainder of the antibody heavy and light chains, near the C-termini, are relatively constant and are known as the constant regions (C regions). The variable regions comprise three hypervariable regions (HVRs) and four relatively conserved framework regions (FRs). The three hypervariable regions determine the specificity of the antibody, and are also known as complementarity determining regions (CDRs). Each light chain variable region (LCVR) and each heavy chain variable region (HCVR) is composed of three CDRs and four FR regions, and the sequential order of the components, from the amino terminus to the carboxy terminus is: FR1, CDR1, FR2, CDR2, FR3, CDR3, and FR4. The three light chain CDR regions, namely the light chain hypervariable regions, are referred to asLCDR1, LCDR2, and LCDR3. The three heavy chain CDR regions, namely the heavy chain hypervariable regions, are referred to asHCDR1, HCDR2 and HCDR3. The number and location of the CDR amino acid residues in the LCVR and HCVR regions of the antibody or antigen binding fragment thereof disclosed herein comply with known Kabat numbering criteria (LCDR1-3, HCDE2-3), or comply with kabat and chothia numbering criteria (HCDR1).

As used herein, "antigen-binding fragment" refers to a Fab fragment, Fab' fragment, F(ab')$_2$ fragment or a single Fv fragment having antigen-binding activity. An Fv antibody is a minimum antibody fragment comprising a heavy chain variable region, a light chain variable region and all of the antigen-binding sites, without the constant region. Generally, an Fv antibody further comprises a polypeptide linker between the VH and VL domains, and is capable of forming a structure required for antigen binding.

As used herein, the term "antigen determinant" refers to the three-dimensional sites, which are distinct on the antigen, that are recognized by the antibody or antigen binding fragment of the present invention.

"Administration" and "treatment," as they apply to animals, human, experimental subjects, cells, tissues, organs, or biological fluid, refer to contact of animals, humans, subjects, cells, tissues, organs, or biological fluids with exogenous medicaments, therapeutic agents, diagnostic agents, or compositions. "Administration" and "treatment" can refer to, e.g., therapeutic, pharmacokinetic, diagnostic, research, and experimental methods. Treatment of cells encompasses contacting cells with an agent, as well as contacting fluid with an agent, where the fluid is in contact with the cells. "Administration" and "treatment" also mean in vitro and ex vivo treatment of, e.g., cells, by an agent, a diagnostic composition, a binding composition, or by other cells. "Treatment," as it applies to human, veterinary, or research subjects, refers to therapeutic treatment, prophylactic or preventative measures, or to research or diagnostic applications. "Treatment" as it applies to human, veterinary, or research subjects, or cells, tissues, or organs, encompasses contacting human or animal subjects, cells, tissues, physiological compartments, or physiological fluid with an IL-17A agonist or an IL-17 A antagonist. "Treatment of cells" also encompasses situations where the IL-17A agonist or IL-17A antagonist is contacted with an IL-17A receptor, e.g., in the fluid phase or colloidal phase, and also encompasses situations where the agonist or antagonist is not contacted with the cells or the receptors.

"Treat" means to administer a therapeutic agent, such as a composition containing any of the binding compounds of the present invention, internally or externally to a patient having one or more disease symptoms for which the agent has known therapeutic activity. Typically, the agent is administered in an amount effective to alleviate one or more disease symptoms in the patient or population to be treated, either by inducing the regression of or inhibiting the progression of such symptom(s) by any clinically measurable degree. The amount of a therapeutic agent that is effective to alleviate any particular disease symptom (also referred to as the "therapeutically effective amount") can vary according to various factors, such as the disease state, age, and weight of the patient, and the ability of the drug to elicit a desired response in the patient.

Four variants of human IL-17 A protein are mentioned herein:

1) As used herein, the terms "human IL-17A (huIL-17A)" and "natural human IL-17A" refer to the mature forms (i.e. residues 24-155) of human IL-17A protein with accession numbers NP 002181 and AAT22064, and to naturally occurring variants and polymorphisms thereof.

2) As used herein, the term "rhIL-17A" refers to a recombinant human IL-17A. This nomenclature is adopted for convenience to refer to various forms of IL-17A, and may not match usage in the literature.

3) As used herein, the term "His-huIL-17A" refers to a recombinant human IL-17A having an N-terminal His tag, "FLAG-huIL-17A" refers to a recombinant human IL-17A having an N-terminal FLAG tag. In some experiments the FLAG-huIL-17A is biotinylated.

4) R&D Systems human IL-17A mentioned herein is a recombinant human IL-17A purchased from R&D Systerms.

As used herein, the term "monoclonal antibody" refers to an antibody secreted by a clone derived from a single cell. Monoclonal antibodies are highly specific and are directed against a single epitope. The cell is not limited to eukaryotic, prokaryotic, or phage clonal cell lines.

The monoclonal antibody herein specifically includes a "chimeric" antibody, in which a portion of the heavy and/or light chain is identical or homologous to the corresponding sequences of antibodies derived from a particular species or belonging to a particular antibody type or subtype, while the remainder of the chain(s) is identical or homologous to the corresponding sequences of antibodies derived from another species or belonging to another antibody type or subtype, as well as fragment of such antibody, as long as they exhibit the desired biological activity.

As used herein, the term "humanized antibody" is a variable region-modified form of the murine antibody according to the present invention, having CDRs derived from (or substantially derived from) a non-human antibody (preferably a mouse monoclonal antibody), and FR regions and constant regions substantially derived from a human antibody; that is, CDR sequences of murine antibody are grafted onto different types of human germline antibody framework sequences. Such framework sequences can be obtained from public DNA databases or published references that include germline antibody gene sequences. For example, germline DNA sequences of human heavy variable region genes and human light chain variable region genes can be found in the human germline sequence database "VBase" (available online at www.mrccpe.com.ac.uk/vbase), as well as found in Kabat, E A, et al. 1991, Sequences of Proteins of Immunological Interest, 5th Ed. Because CDR sequences are responsible for most antibody-antigen interactions, it is feasible to construct an expression vector to express a recombinant antibody that can mimic specific feature of a naturally occurring antibody.

"Optional" or "optionally" means that the following event or situation can but does not necessarily occur, and the description includes the instances in which the event or situation does or does not occur. For example, "optionally contains 1-3 antibody heavy chain variable regions" means that the antibody heavy chain variable region with specific sequences can be, but is not necessarily, present, and if it is present, there can be 1, 2 or 3 antibody heavy chain variable regions.

Transformation of the host cell with the recombinant DNA can be carried out by conventional techniques well known to those skilled in the art. The obtained transformants can be cultured by using conventional methods to express the polypeptide encoded by the gene of the invention. Culture medium can be selected from various conventional culture mediums based on the host cells used. The host cells are grown under the appropriate conditions.

II. Antibodies Specific for Human IL-17A

The present invention provides engineered anti-IL-17A antibodies and uses thereof to treat various inflammatory, immune and proliferative disorders, including rheumatoid arthritis (RA), osteoarthritis, rheumatoid arthritis osteoporosis, inflammatory fibrosis (e.g., scleroderma, lung fibrosis, and cirrhosis), inflammatory bowel disorders (e.g., Crohn's disease, ulcerative colitis and inflammatory bowel disease), asthma (including allergic asthma), allergies, COPD, multiple sclerosis, psoriasis and cancer.

Any suitable method for generating monoclonal antibodies can be used to generate the anti-IL-17A antibodies of the present invention. For example, an animal recipient can be immunized with a linked or naturally occurring IL-17A homodimer, or a fragment thereof. Any suitable method for immunization can be used. Such methods can include adjuvants, other immunostimulants, repeated booster immunizations, and the use of one or more immunization routes.

Any suitable form of IL-17A can be used as the immunogen (antigen) for the generation of the non-human antibody specific for IL-17A, and the antibody can be screened for its biological activity. The eliciting immunogen can be full-length mature human IL-17A, including naturally occurring homodimers, or peptides thereof encompassing a single epitope or multiple epitopes. The immunogen can be used alone or in combination with one or more immunogenicity enhancing agents known in the art. The immunogen can be purified from a natural source or produced in genetically modified cells. DNA encoding the immunogen can be derived from genomic or non-genomic (e.g., cDNA) DNA. Suitable genetic vectors can be used to express the DNAs encoding the immunogen, and the vectors can include but are not limited to adenoviral vectors, adeno-associated viral vectors, baculoviral vectors, plasmids, and non-viral vectors.

An exemplary method for producing anti-human IL-17A antibodies of the present invention is described at Example 1.

III. Humanization of IL-17A-Specific Antibodies

The humanized antibody can be selected from any type of immunoglobulins, including IgM, IgG, IgD, IgA, and IgE. In one embodiment, the antibody is an IgG antibody. Any isotype of IgG can be used, including IgG1, IgG2, IgG3, and IgG4. Variants of the IgG isotypes are also contemplated. The humanized antibody can comprise sequences derived from more than one type or isotype. Optimization of the necessary constant domain sequences to generate the desired biological activity is readily achieved by screening the antibodies in the biological assays described in the Examples below.

Likewise, any type of light chain can be used in the compounds and methods herein. Specifically, kappa (κ), lambda (λ), or a variant thereof is useful in the present compounds and methods.

An exemplary method of humanizing anti-human IL-17A antibodies of the present invention is described at Example 2.

DETAILED DESCRIPTION OF THE INVENTION

Hereinafter, the present invention is further described with reference to examples. However, the scope of the present invention is not limited thereto.

In the examples of the present invention, where specific conditions are not described, the experiments are generally conducted under conventional conditions, or under conditions proposed by the material or product manufacturers. See Sambrook et al., Molecular Cloning, A Laboratory Manual, Cold Spring Harbor Laboratory; Current Protocols in Molecular Biology, Ausubel et al, Greene Publishing Associates, Wiley Interscience, NY. Where the source of the reagents is not specifically given, the reagents are commercially available conventional reagents.

Example 1: Mouse Anti-Human IL-17A Monoclonal Antibody

Monoclonal antibodies against human IL-17A were obtained as follows. 6-8 week old female BALB/c mice (Shanghai Super B&K Laboratory Animal Corp. Ltd, laboratory animal production Certificate No: SCXK (HU) 2008-0016) and 6-8 week old female SJL mice (Beijing Weitong Lihua Experimental Animal Technology Co. Ltd, laboratory animal production Certificate No: SCXK (Beijing) 2012-0001) were divided into two groups, a high dose group and a low dose group. 10 BALB/c mice and 10 SJL mice were in each group.

The high and low dose groups were serially immunized with natural hIL-17A variants (His-hIL-17A; the amino acid sequence of hIL-17A refers to human IL-17A protein Genbank accession number NP-002181, and the resulting protein was purified by Ni affinity column (Superdex) and 75SEC, sequentially) that were His-tagged at the N-terminus and generated using a HEK293E (293-EBNA, Invitrogen, Lot Num: 493985) expression system. The inoculations were performed on days 0, 14, 35, and 56.

On day 0, the high dose group was administered with His-huIL-17A, at 500 µg/mouse, via subcutaneous (s.c.) injection, and Complete Freund's Adjuvant (CFA) was administered via intraperitoneal (i.p.) injection at the same time. On days 14 and 35, 25 μg/mouse His-hIL-17A was administered via s.c. injection, and Incomplete Freund's Adjuvant (IFA) was administrated via i.p. injection at the same time. On day 56, before fusing the splenocytes, a booster immunization was performed by i.p. injection of 25 μg/mouse His-hIL-17A dissolved in saline. The time schedule and method for the immunization of the low dose group was the same as those for high dose group, except that the administered dose of His-hIL-17A on day 0 was 10 μg/mouse, and the administered dose of His-hIL-17A on days 14, 35, and 56 was 5 μg/mouse.

Blood tests were performed on days 22 and day 43. Mouse serum was tested using an ELISA Test described in Test Example 1 to determine the antibody titers in the serum. On day 56, mice with higher antibody titers in their serum were selected for splenocyte fusion. Hybridoma cells were obtained by fusing splenic lymphocyte with myeloma Sp2/0 cells (ATCC® CRL-8287™) using an optimized PEG-mediated fusion procedure.

The procedures for immunization were as follows:
Scheme 1, high dose, 10 Balb/c mice and 10 SJL mice—

| Day | |
|---|---|
| Day 0 | Pre-blood sampling 15-30 μL serum/mouse; primary immunization, IP, CFA 50 μg/mouse |
| 14 | Boost 1 (booster immunization 1): IP, IFA 25 μg/mouse |
| 21 | Blood sampling (15-30 μL serum/mouse) |
| 22 | ELISA test |
| 35 | Boost 2 (booster immunization 2): IP, IFA 25 μg/mouse |
| 42 | Blood sampling (15-30 μL serum/mouse) |
| 43 | ELISA test |
| 44 | Data analysis and interim conclusion |
| 56 | Pre-fusion booster immunization, IP, 25 μg/mouse of saline |

Scheme 2, low dose—

| Day | |
|---|---|
| Day 0 | Pre-blood sampling 15-30 μL serum/mouse; primary immunization, IP, CFA 10 μg/mouse |
| 14 | Boost 1 (booster immunization 1): IP, IFA 5 μg/mouse |
| 21 | Blood sampling (15-30 μL serum/mouse) |
| 22 | ELISA test |
| 35 | Boost 2 (booster immunization 2): IP, IFA 5 μg/mouse |
| 42 | Blood sampling (15-30 μL serum/mouse) |
| 43 | ELISA test |
| 44 | Data analysis and interim conclusion |
| 56 | Pre-fusion booster immunization, IP, 5 μg/mouse of saline |

Primary screening of the resulting hybridomas was performed by an antigen-antibody indirect ELISA test in Test Example 1. Monoclonal cell lines were obtained by limiting the dilution of positive cell lines.

The obtained monoclonal cell lines were further analyzed by methods including:

1. A receptor blocking test (see Test Example 2): the results, shown in Table 5, revealed that a monoclonal cell line, IL17-mAb049, having superior activity compared to the positive control was obtained;
2. Affinity test (see Test Example 3): the results, shown in Table 6, revealed that the monoclonal cell line IL17-mAb049 obtained in the present invention demonstrated comparable or improved activity when compared to the positive control;
3. Bioassay at cellular level (GROα analysis, see Test Example 4): the results, shown in Table 8, revealed that the monoclonal cell line IL17-mAb049 obtained in the present invention demonstrated comparable or improved activity when compared to the positive control.

Twelve of the monoclones were studied further. One lead monoclone (lead mAb), IL17-mAb049, was selected based on epitope grouping and biological activity testing. The specific sequences of the heavy chain (VH) and light chain (LH) of the murine IL-17A mouse antibody mAb049 (IL-17mAb) were as follows:

IL-17 mAb049 VH
SEQ ID NO: 1
HVQLQQSGADLVRPGASVTLSCKASGYIFTDYEVHWVKQTPVHGLEWIGV

IDPGTGGVAYNQKFEGKATLTADDSSNTAYMELRSLTSEDSAVYYCTRYS

LFYGSSPYAMDYWGQGTSVTVSS

IL-17mAb 049 VL
SEQ ID NO: 2
QIVLTQSPAIMSASPGEKVTITCSASSSVNYMHWFQQKPGTSPKLWIYRT

SNLASGVPVRFSGSGSGTSYSLTISRMEAEDAATYYCQQRSSYPWTFGGG

TNLEIK

Example 2: Humanization of Murine-Anti-Human IL-17A Antibodies

The humanization of murine-anti-human IL-17A monoclonal antibody mAb049 was performed essentially as described in many publications known to those skilled in the art. Briefly, human constant domains were used to replace the parental (murine antibody) constant domains. The human germline sequences used for humanization were selected according to homology between the murine antibody and the human antibody.

1. CDR Regions of Murine Anti-IL-17A Antibody

VH/VL CDR amino acid residues were identified and annotated by the Kabat numbering system. CDR sequences of murine mAb049 in the present invention are listed in the following table:

TABLE 1

CDR sequences of mouse anti-IL-17A antibody

| | | mAb049 | |
| --- | --- | --- | --- |
| | Domain | Sequence | SEQ ID NO |
| VH | CDR1 | DYEVH | 10 |
| | CDR2 | VIDPGTGGVAYNQKFEG | 11 |
| | CDR3 | YSLFYGSSPYAMDY | 12 |
| VL | CDR1 | SASSSVNYMH | 13 |
| | CDR2 | RTSNLAS | 14 |
| | CDR3 | QQRSSYPWT | 15 |

2. Selection of Human Germline FR Sequences

On the basis of characteristic structures of the obtained murine antibody VH/VL CDRs, the sequences of the heavy and light chain variable regions were compared to an antibody database. Human germline heavy chain VH1-18 (SEQ ID NO: 3) and light chain A10 (SEQ ID NO: 4) with high homology were selected based on their high degree of homology, and were used as humanized FR sequences. The specific sequences were as follows:

VH1-18

SEQ ID NO: 3

QVQLVQSGAEVKKPGASVKVSCKASGYTFTSYGISWVRQAPGQGLEWMGW

ISAYNGNTNYAQKLQGRVTMTTDTSTSTAYMELRSLRSDDTAVYYCAR

A10

SEQ ID NO: 4

EIVLTQSPDFQSVTPKEKVTITCRASQSIGSSLHWYQQKPDQSPKLLIKY

ASQSFSGVPSRFSGSGSGTDFTLTINSLEAEDAATYYCHQSSSLP

3. Design of Humanized Antibodies:

The amino acid residues forming the ring conformation and the VH interface were determined. Using that information, a Q1E mutation was introduced to eliminate the formation of N-terminal pyroglutamic acid. Other mutations were made to maintain consistency within the selected VH family, to maintain the characteristic CDR structure and VH/VL interface, and to avoid the N-glycosylation pattern (N-{P}-S/T) present in the humanized structure.

The design of the humanized mutations in the variable regions of the murine antibody mAb049 are summarized as follows:

TABLE 2

Design of humanized sites in murine antibody mAb049

| | Design of humanized sites in heavy chain VH (VH1-18) + JH4/FW4 | | Design of humanized sites in light chain Vk(A10) + JK2/FW4 |
|---|---|---|---|
| Mutation type | Humanized back mutation site | Mutation type | Humanized back mutation site |
| Hu049 VH.1 | CDR-grafted* | Hu049 Vk.1 | CDR-grafted* |
| Hu049 VH.1A | A93T | Hu049 Vk.1A | F71Y |
| Hu049 VH.1B | A93T, T71A | Hu049 Vk.1B | F71Y, K49Y |
| Hu049 VH.1C | A93T, T71A, M48I | Hu049 Vk.1C | F71Y, K49Y, Y36F, L47W |
| Hu049 VH.1D | A93T, T71A, M48I, V67A, M69L, T73D, S76N | | |

NOTE:
For example, A93T denotes a back mutation from A to T at position 93 according to Kabat numbering system.
* Indicates that the murine antibody CDR was implanted into human germline FR sequences.

TABLE 3

Murine antibody mAb049 humanized sequences

| | Hu049 VH.1 | Hu049 VH.1A | Hu049 VH.1B | Hu049 VH.1C | Hu049 VH.1D |
|---|---|---|---|---|---|
| Hu049 VK.1 | Hu049-1 | Hu049-2 | Hu049-3 | Hu049-4 | Hu049-5 |
| Hu049 VK.1A | Hu049-6 | Hu049-7 | Hu049-8 | Hu049-9 | Hu049-10 |
| Hu049 VK.1B | Hu049-11 | Hu049-12 | Hu049-13 | Hu049-14 | Hu049-15 |
| Hu049 VK.1C | Hu049-16 | Hu049-17 | Hu049-18 | Hu049-19 | Hu049-20 |

NOTE:
This table shows various sequence combinations of different mutations. For example, Hu049-8 indicates that two mutations (Hu049VK.1A and Hu049VH.1B) are present in the humanized murine antibody mAb049, and so on.

4. Expression and Purification of Humanized Antibody

The above-mentioned antibodies were cloned, expressed and purified by genetically recombinant methods. Humanized antibodies were assessed by ELISA, a receptor binding inhibition assay, Biacore, a cell viability test etc., and those demonstrating desirable properties were selected. Specific antibodies are indicated in the following table:

TABLE 4 components of humanized IL-17A antibody

| Antibody | Heavy chain | SEQ ID NO | Light chain SEQ ID NO |
|---|---|---|---|
| Hu049-17 | Hu049-17.VH | SEQ ID NO: 5 | Hu049 VL SEQ ID NO: 9 |
| Hu049-18 | Hu049-18.VH | SEQ ID NO: 6 | |
| Hu049-19 | Hu049-19.VH | SEQ ID NO: 7 | |
| Hu049-20 | Hu049-20.VH | SEQ ID NO: 8 | |

Specific sequences of the humanized antibody mAb049 are listed below:

Hu049-17.VH

SEQ ID NO: 5

EVQLVQSGAEVKKPGASVKVSCKASGYTFTDYEVHWVRQAPGQGLEWMGV

IDPGTGGVAYNQKFEGRVTMTTDTSTSTAYMELRSLRSDDTAVYYCTRYS

LFYGSSPYAMDYWGQGTLVTVSS

Hu049-18.VH

SEQ ID NO: 6

EVQLVQSGAEVKKPGASVKVSCKASGYTFTDYEVHWVRQAPGQGLEWMGV

IDPGTGGVAYNQKFEGRVTMTADTSTSTAYMELRSLRSDDTAVYYCTRYS

LFYGSSPYAMDYWGQGTLVTVSS

Hu049-19.VH

SEQ ID NO: 7

EVQLVQSGAEVKKPGASVKVSCKASGYTFTDYEVHWVRQAPGQGLEWIGV

IDPGTGGVAYNQKFEGRVTMTADTSTSTAYMELRSLRSDDTAVYYCTRYS

LFYGSSPYAMDYWGQGTLVTVSS

Hu049-20.VH

SEQ ID NO: 8

EVQLVQSGAEVKKPGASVKVSCKASGYTFTDYEVHWVRQAPGQGLEWIGV

IDPGTGGVAYNQKFEGRATLTADDSTNTAYMELRSLRSDDTAVYYCTRYS

LFYGSSPYAMDYWGQGTLVTVSS

Hu049VL

SEQ ID NO: 9

EIVLTQSPDFQSVTPKEKVTITCSASSSVNYMHWFQQKPDQSPKLWIYRT

SNLASGVPSRFSGSGSGTDYTLTINSLEAEDAATYYCQQRSSYPWTFGQG

TKLEIKR

Example 3: In Vivo Pharmacokinetics and Pharmacodynamics Tests of Humanized Anti-IL-17 Antibody Human IL-17 can bind to and stimulate the mouse IL-17 receptor, resulting in increased expression and subsequent secretion of chemokines KC (CXCL1) in male mice. Experiments covering various time points and various doses were performed to identify an optimal dose of human IL-17 and an optimal time point for KC induction (see Test Example 5). These experiments showed that 150 mg/kg of human IL-17 induces the highest level of KC in mouse serum 2 hours after IL-17 administration. Full-length antibodies of the present invention were intravenously administered to mice at the concentrations of 3, 30, 300, 3000 μg/kg, 20 hours before the subcutaneous injection of human IL-17. Two hours after human IL-17 administration, the mice were sacrificed, and KC levels were determined by ELISA according to the manufacturer's specification (Mouse CXCL1/KC Quantikine ELISA Kit, R & D SYSTEM, #SMKC00B). An isotype-matched antibody was used as a negative control. Antibodies block the ability of human IL-17 to stimulate the mouse IL-17 receptor, resulting in the inhibition of increased KC expression in a dose-dependent manner in mice. Compared to the ineffective control antibody, the antibody Hu049-18 of the present invention reduced the average KC level to about ⅙ under the described conditions at the dose of 3000 μg/mice.

Serum pharmacokinetics in rats and macaque was determined after intravenous or subcutaneous administration of the antibody Hu049-18 of the present invention (see Test Example 6). In rats, the half-life was 9.91 days after intravenous administration of 5 mg/kg, and the half-life was 11.5 days after subcutaneous administration of 5 mg/kg. In macaque, the half-life was 24.4 days after intravenous administration of 1 mg/kg.

TEST EXAMPLES

Test Example 1: Indirect ELSIA

Purpose:

An indirect ELISA method was used to ensure the selection of antibodies that can recognize a conformational epitope, and for screening the mouse hybridomas from Example 1 of the present invention.

Materials:

Human IL-17A (hIL-17A) was cloned according to methods known in the art, using the human IL-17A protein sequence with the Genbank Accession No. NP-002181, and the cloned sequence was transiently transfected into HEK293E cells for expression.

Human IL-17A/F (heterodimer, hIL-17A/F) was cloned according to methods known in the art, using the human IL-17A protein sequence with the Genbank Accession No. NP-002181 and the human IL-17F protein sequence with the Genbank Accession No. NP_443104, and the cloned sequence was transiently transfected into HEK293E cells for expression.

The positive controls, murine anti-IL-17 antibodies from Lilly and Novartis (Lilly mAb, Novartis mAb) were cloned using the murine sequences disclosed in U.S. Pat. No. 7,838,638B2 (LY 2439821) and U.S. Pat. No. 7,807,155B2 (AIN 457), respectively, and the cloned sequence was transiently transfected into HEK293E cells for expression.

Murine mAbs antibodies derived from the mouse hybridoma disclosed in Example 1 of the present invention.

Protocol:

1. Microtitration plates were directly coated with 1 μg/ml of streptavidin, and incubated at 4° C. overnight;

2. Microtitration plates were blocked with 300 μl of PBST containing 2% BSA (v/v), and thermostatically incubated at 37° C. for 1 h, and uncoated wells were blocked as controls;

3. The plates were washed with PBST three times, and all of the washing operations were performed using a Biotek (Elx 405) automatic washer;

4. 100 μl of PBS containing hIL-17A or hIL-17A/F (1 μg/ml) were added to each well, and the plates were thermostatically incubated at 37° C. for 1 h;

5. The plates were washed with PBST three times.

6. The positive controls, Lilly mAb and Novartis mAb, or murine mAbs antibodies of the present invention were titrated at a 1:5 dilution, with an initial concentration of 1 μg/ml. 100 μl of diluted positive control or murine antibody of the present invention were added to each well, and the plates were thermostatically incubated at 37° C. for 1 h. Each concentration was tested in duplicate;

7. The plates were washed with PBST three times;

8. 100 μl of HRP anti-murine secondary antibody (Santa Cruz Cat. No. sc-2005) (1:5000) were added to each well, and the plates were thermostatically incubated at 37° C. for 1 h;

9. The plates were washed with PBST three times. 100 μl of TMB Substrate were added to each well, and the plates were thermostatically incubated at 37° C. for 5 min. The reaction was stopped by the addition of 100 μl 2M $H_2SO_4$ to each well;

10. The OD value at a wavelength of 450 nm was read on an ELISA microplate reader (Molecular Devices, Spectra Max).

11. The OD values of the murine mAb antibodies were compared to those of the positive controls. Monoclonal cell lines with a ratio greater than 1, including IL17-mAb049, were screened.

Test Example 2: IL-17 Receptor Blocking Assay (RBA)

Purpose:

The purpose of the receptor blocking assay was to select the antibodies capable of blocking the binding of IL-17 to the IL-17 receptor (e.g., hIL-17RA). The test is based on a functional test, and it can be used for hybridoma high-throughput screening.

Materials and Equipment:

Anti-human Fc antibody (goat anti-human IgG-Fc fragment specific antibody (available from Jackson Immunoresearch, 109-005-008))

Human IL-17RA-Fc was cloned according to methods known in the art, using the human IL-17A receptor amino acid sequence with the Genbank ID No. ADY18334.1, and the cloned sequence was transiently transfected into HEK293E cells for expression, wherein the Fc fragments were obtained from human IgG1.

The positive controls, murine anti-IL-17 antibodies from Lilly and Novartis (Lilly mAb, Novartis mAb) were cloned using the murine sequences disclosed in U.S. Pat. No. 7,838,638B2 (LY 2439821) and U.S. Pat. No. 7,807,155B2 (AIN 457), respectively, and the cloned sequence was transiently transfected into HEK293E cells for expression.

mIgG: Murine IgG (Millipore Cat. No. PP54), used as a negative control

ELISA plate reader: Molecular Devices, Spectra Max

Murine monoclonal cell strains obtained from Example 1 of the present invention.

Protocol:

1. Microtitration plates were directly coated with 10 μg/ml of Anti-human Fc antibody, and incubated at 4° C. overnight;

2. Microtitration plates were blocked with 300 μl of PBST containing 2% BSA (v/v), and thermostatically incubated at 37° C. for 1 h, and uncoated wells were blocked as controls;

3. The plates were washed with PBST three times, and all of the washing operations were performed using a Biotek (Elx 405) automatic washer;

4. 100 μl of PBS containing IL-17 RA-Fc (60 ng/ml) were added to each well, and the plates were thermostatically incubated at 37° C. for 2 h;

5. The plates were washed with PBST three times.

6. The positive controls, Lilly mAb and Novartis mAb, or antibodies of the present invention were diluted at a 1:5 ratio, with an initial concentration of 40 μg/ml. mIgG was diluted using the same method. 50 μl of diluted positive control, murine antibody of the present invention, or mIgG were added to each well, and, 50 μl of 0.2 nM biotin-labeled IL-17A were added to the wells containing diluted positive control or the antibody of the present invention, mixed gently and the plates were thermostatically incubated at 37° C. for 1 h.

7. The plates were washed with PBST three times;

8. 100 μl of HRP-labeled streptavidin complex (1:5000) were added to each well, and the plates were thermostatically incubated at 37° C. for 1 h;

9. The plates were washed with PBST three times. 100 μl of TMB Substrate were added to each well, and the plates were thermostatically incubated at 37° C. for 5 min. The reaction was stopped by the addition of 100 μl 2M $H_2SO_4$ to each well;

10. The OD value at a wavelength of 450 nm was read on an ELISA microplate reader.

11. The $IC_{50}$ value of the antibody being tested was calculated to measure blocking of the binding of IL-17 to IL-17 receptor.

The $IC_{50}$ value (the antibody concentration when the OD value reduced 50%, i.e. RBA) was obtained according to the gradient curve of OD values versus antibody concentration.

Experimental Results:

According to the above method, the hybridoma obtained in Example 1 was screened to obtain a murine monoclonal antibody, designated IL17-mAb049, and the results were as follows:

TABLE 5

| Antibody | huIL-17 RBA □ (nM) |
|---|---|
| Lilly mAb | 0.17 |
| Novartis mAb | 1.56 |
| IL17-mAb049 | 0.07 |

Conclusion: The murine antibody IL17-mAb 049 screened from the hybridomas showed improved activity compared to the positive control antibodies, Lilly mAb and Novartis mAb.

Test Example 3: Affinity Test

Purpose:

The BIACORE method was used in the experiment for determining antigen-antibody binding kinetics and affinity.

Materials and Equipments:

1.1 Proteins:

Human IL-17A (hIL-17A) was cloned according to methods known in the art, using the human IL-17A protein sequence with the Genbank Accession No. NP-002181, and the cloned sequence was transiently transfected into HEK293E cells for expression.

Human IL-17A/F (heterodimer, hIL-17A/F) was cloned according to methods known in the art, using the human IL-17A protein sequence with the Genbank Accession No. NP-002181 and human IL-17F protein sequence with the Genbank Accession No. NP_443104, and the cloned sequence was transiently transfected into HEK293E cells for expression.

Mouse IL-17A (Mu IL-17A) and rat IL-17A (Rat IL-17A) were cloned according to methods known in the art, using the mouse IL-17A protein sequence with the Genbank Accession No. NP_034682 and the rat IL-17A protein sequence with the Genbank Accession No. NP_001100367, respectively, and the cloned sequence was transiently transfected into HEK293E cells for expression.

The positive controls, murine anti-IL-17 antibodies from Lilly and Novartis (Lilly mAb, Novartis mAb) were cloned using the murine sequences disclosed in U.S. Pat. No. 7,838,638B2 (LY 2439821) and U.S. Pat. No. 7,807,155B2 (AIN 457), respectively, and the cloned sequence was transiently transfected into HEK293E cells for expression.

The positive control, Lilly humanized anti-IL-17 antibody (Lilly mAb(hu)), was cloned using the humanized sequences disclosed in U.S. Pat. No. 7,838,638B2 (LY 2439821), and the cloned sequence was transiently transfected into HEK293E cells for expression.

Murine monoclonal cell strains obtained from Example 1 of the present invention.

Humanized IL-17 antibodies obtained from Example 2 of the present invention.

1.2 BIACORE Model: BIACORE X 100, GE;

1.3 BIACORE Chips and Reagents (Trade Names are Listed Hereafter, No Acknowledged Translation):

| Materials and Reagents | Company | Product list |
|---|---|---|
| 1. Sensor Chip CM5 Research Grade | GE Healthcare | BR-1000-14 |
| 2. Amine Coupling Kit | GE Healthcare | BR-1000-50 |
| 3. HBS buffer BIA Certified | GE Healthcare | BR-1001-88 |
| 4. Acetate (100 ml) | GE Healthcare | BR-1003-51 |
| 5. Mouse Antibody Capture Kit | GE Healthcare | BR-1008-38 |
| 6. Regeneration buffer Glycine 1.5 | GE Healthcare | BR-1003-54 |
| 7. BIAmaintenance Kit | GE Healthcare | BR-1006-66 |

Protocol:

1. An antibody of the present invention was immobilized on a CM5 chip. A 1:1 solution of 50 mM NETS: 200 mM EDC was prepared and injected into FC2 (Flow cell 2) channel at a rate of 10 μL/min, for 7 min, to activate the CM5 sensor chip. The Antibody of the present invention was dissolved in 10 mM sodium acetate buffer at a concentration of 30 μg/ml, pH 5.0, and injected into the activated chip (HBS-EP mobile phase buffer: 10 mM HEPES, 150 mM NaCl, 3.4 mM EDTA, 0.005% surfactant P20, pH 7.4) at a rate of 5 μL/min. 1M ethanolamine was injected at a rate of 10 μL/min, for 7 min, to seal the remaining activated coupling positions. About 8000RU was generated.

2. Binding kinetics Test: FC1 (Flow cell 1) was used as the reference channel, FC2 (Flow cell 2) was used as the sample channel, and murine or humanized control antibody or the antibody of the present invention was captured in the FC2 channel at 300RU, followed by the injection of different concentrations of IL-17 (including hIL-17A, MuIL-17, Rat IL-17). Cycle conditions were: injecting analytes into all FC channels at 30 μl/min for 3 min, dissociation for 20 min, injecting 10 mM Glycine, pH 1.5, for 60 s (at rate of 10 μl/min) for surface regeneration. The difference between the signal with captured antibody and the signal without captured antibody was calculated using Biacore X100 evaluation software ver 2.0 (Biacore), and the running buffer was 10 mM Hepes, 650 mM NaCl, 3 mM EDTA, 0.05% Tween-20.

Experimental Results:

1. Hybridomas obtained in Example 1 were tested using the above method, and the results were as follows:

TABLE 6

| Antibody | 人 IL-17A □ KD (M) |
|---|---|
| Lilly mAb | 2.18E−11 |
| Novartis mAb | 4.24E−10 |
| IL17-mAb049 | 2.62E−11 |

Conclusion: The affinity of the murine antibody IL17-mAb 049 obtained from hybridomas is equivalent to that of the positive control Lilly mAb antibody, and is stronger than that of the positive control Novartis mAb antibody.

2. Humanized IL-17 antibodies obtained from Example 2 were tested using the above method, and the results were as follows:

TABLE 7

| Humanized antibody | Human IL-17A □ KD (M) | Mu IL-17 KD (M) | Rat IL-17 □ KD (M) |
|---|---|---|---|
| Lilly's mAb (hu) | 1.48E−11 | | |
| Hu049-17 | <1 pM | 1.37E−10 | 1.06E−09 |
| Hu049-18 | <1 pM | 6.81E−11 | 4.77E−10 |
| Hu049-19 | 2.68E−12 | 7.71E−11 | 6.00E−11 |

Conclusion: The affinity of the humanized antibody 10 times higher than that of Lilly's positive control antibody (1.48E-11M).

Test Example 4: Cellular Bioassay (GROα Assay)

Purpose:
The following experiment was intended to assess the cellular biological activity of the anti-IL-17A antibody in inhibiting IL-17-stimulated secretion of GROα from Hs27 cells.

Materials and Equipment:
Hs27 cells: ATCC Cat. No. CRL-1634 (Note: cells cultured for more than six weeks are not recommended for the bioassay);
Hs27 cell culture medium: DMEM+10% FBS
DMEM: ATCC Cat. No. 30-2002;
FBS: GIBCO Cat. No. 10099, lot 8122818;
Recombinant human IL-17A (rhIL-17A): R&D Systems Cat. No. 317-ILB, lot SOA161109B;
Recombinant human IL-17A/F (rhIL-17A/F): R&D System Cat No. 5194-IL/CF, lot RXT101109A;
Human CXCL1/GRO alpha Quantikine PharmPak kit: R&D system Cat. No. PDGR00
Equipment: Biotek ELx808 microplate reader.
Murine monoclonal cell strain obtained from Example 1 of the present invention.
Humanized IL-17 antibody obtained from Example 2 of the present invention.

Protocol:
1. Hs27 Cell Culture:
Hs27 cells were cultured in 50 ml of DMEM +10% FBS medium in T175 flasks, and the cells (at a density of about 90%) were diluted at a ratio of 1:3 every 3 days. The cells were used for the bioassay within a month, or they were re-thawed from liquid nitrogen. The re-thawed cells were cultured for at least a week before use in the bioassay.

2. Bioassay (IL-17A) Experimental Procedure
2.1 Hs27 cells were centrifuged at 950 rpm for 4 min (for complete removal of trypsin-EDTA) and collected. Cell viability was analyzed using a trypan blue stain, and only cells with >80% vitality were used for the experiment;
2.2 Medium was added into a 96-well plate at 50 μl/well;
2.3 Hs27 cells were diluted with DMEM+10% FBS and added into a 96-well plate at a density of 10000 cells/50 μl/well;
2.4 25 μl of the IL-17 human antibody were added into each well in duplicate, and the antibody was diluted at a ratio of 1:3 with an initial concentration of 10 nM;
2.5 25 μl of recombinant human IL-17A were added into each well with a final concentration of 0.3 nM, and the 96-well plate was centrifuged at 500 rpm for 1 min;
2.6 Cells were thermostatically incubated at 37° C. for 17 h;
2.7 Cell culture supernatant was collected, and the concentration of GROα was detected in the supernatant using a human CACL1/GRO alpha Quantikine kit (according to the manufacturer's instructions);
3. Experimental procedure of the Bioassay (IL-17A/F):
The procedure of IL-17A/F bioassay was similar to that of IL-17A bioassay, except that IL-17A was substituted by IL-17A/F.

Experimental Results:
1. The hybridoma obtained in Example 1 was tested according to the above methods, and the results were as follows:

TABLE 8

| Antibody | huIL-17 Bioassay (IC50, nM) | huIL-17A/F Bioassay (IC50, nM) |
|---|---|---|
| Lilly mAb | 0.04 | 0.69 |
| Novartis mAb | 0.22 | 1.15 |
| IL17-mAb049 | 0.04 | 0.46 |

Conclusion: The biological activity of the IL17-mAb049 antibody obtained from the hybridoma is equivalent to that of the positive control Lilly mAb antibody, and is higher than that of the positive control Novartis mAb antibody.

2. Thumanized antibodies obtained from Example 2 were tested according to the above methods, and the results were as follows:

TABLE 9

| Antibody | huIL-17 Bioassay (IC50, nM) | huIL-17A/F Bioassay (IC50, nM) | Cyno IL-17A |
|---|---|---|---|
| Lilly's mAb (hu) | 0.033 | 0.83 | |
| Hu049-17 | 0.061 | 0.406 | 0.03 |
| Hu049-18 | 0.04 | 0.684 | 0.033 |
| Hu049-19 | 0.066 | 0.411 | 0.039 |
| Hu049-20 | 0.065 | 0.674 | 0.028 |

Conclusion: These results indicate that all of the humanized antibodies exhibit cellular biological activity. Hu049-17, 18, 19 and 20 have IC50 values (0.04 nM-0.066 nM) similar to that of the positive control antibody (0.04 nM). In addition, these antibodies display cross-reaction with cynomolgus IL-17A (IC50 is 0.03 nM-0.039 nM). The activity against human IL-17A/F is about 10 times weaker than that against IL-17A.

Test Example 5: Neutralization Test of Human IL-17 In Vivo

Purpose:
The aim of the in vivo neutralization test is to verify that the antibodies of the invention can block the in vivo the binding of IL-17 to the IL-17 receptor (e.g., hIL-17RA), thereby inhibiting the CXCR1 expression induced by IL-17.

Materials and Equipment:

Protein: Human IL-17A (hIL-17A) was cloned according to methods known in the art, using the human IL-17A protein sequence with the Genbank Accession No. NP-002181, and the cloned sequence was transiently transfected into HEK293E cells for expression.

The positive control, Lilly humanized anti-IL-17 antibody (Lilly mAb (hu)), was cloned using humanized sequence disclosed in U.S. Pat. No. 7,838,638B2 (LY 2439821), and the cloned sequence was transiently transfected into HEK293E cells for expression.

Human IgG (HuIgG): (Millipore Cat. No. AG711).

Animals: 7-week-old C57/B6 male mice (purchased from SINO-BRITSH SIPPR/BK LAB. ANIMAL LTD., CO, Certificate No.: SOCK (Shanghai) 2008-0016), 6 mice per group.

Reagents: Ab dilution solution: citrate buffer (pH 5.0): 10 mM sodium citrate, 50 mM NaCl hIL-17A dilution solution: PBS (sodium phosphate buffer, pH 7.2).

Mouse CXCL1/KC Quantikine ELISA Kit, 6-well plates, R&D SYSTEM, #SMKC00B.

Protocol:

1) Mice were divided into 15 groups, with 6 mice in each group.

2) 100 uL of Hu049-18 or control antibody (HuIgG or Lilly mAb (hu)), or a diluted solution thereof, was intraperitoneally (I.P.) administered to each mouse, and administration doses of the antibody were 3000 µg/kg, 300 µg/kg, 30 µg/kg and 3 µg/kg.

3) 20 hours later, each mouse was subcutaneously (SC) injected with 100 uL of 150 µg/kg hIL-17A.

4) 2 hours later, blood samples were collected and incubated at room temperature for 2 hours, until coagulation, or at 2-8° C. overnight, until coagulation, and the samples were then centrifuged at 2000×g for 20 min. The supernatant was discarded, and analysis was performed immediately or aliquots of sample were stored at −20° C. Repeated freezing and thawing was avoided.

5) Samples obtained from Step 4 were analyzed using a mouse CXCL1/KC Quantikine ELISA Kit.

Experimental Results:

Humanized antibody Hu049-18 obtained from Example 2 was tested according to the above method, and the results were as follows:

TABLE 10

| Antibody (injection dosage 3000 µg/mouse) | KC mean value (pg/mll) |
|---|---|
| HuIgG | 937 |
| Lilly mAb(hu) | 158 |
| Hu049-18 | 145 |

Conclusion: Compared to the negative control antibody, the Hu-049-18 antibody of the present invention reduced the average KC level by about ⅙ at a dose of 3000 µg/mice under the described condition.

Test Example 6: Determination of the Half-Life (T1/2) of the Antibodies In Vivo

Purpose:

To determine the pharmacokinetics parameters of the Hu049-18 antibody of the present invention in rats or cynomolgus monkeys in vivo.

Materials and Reagents:

Protein: Human IL-17A (hIL-17A) was cloned according to methods known in the art, using the human IL-17A protein sequence with the Genbank Accession No. NP-002181, and the cloned sequence was transiently transfected into HEK293E cells for expression.

The positive control, Lilly humanized anti-IL-17 antibody (Lilly mAb (hu)), was cloned using the humanized sequence disclosed in U.S. Pat. No. 7,838,638B2 (LY 2439821), and the cloned sequence was transiently transfected into HEK293E cells for expression.

Human IgG (HuIgG): Human IgG Polyclonal, Millipore Cat. No. AG711

Animals: 230-250 g SD male rats (purchased from Shanghai SLAC laboratory Animal Co., Ltd., Certificate No: SCXK (Shanghai) 2007-0005), were divided into two groups: an intravenous injection (IV) group (dorsum of foot), and a subcutaneous injection (SC) group; 5 rats were in each group.

Macaque: 2-3 kg cynomolgus monkeys (Hainan Jingang Biotechnology Co., Ltd. Certificate No: SCXK (HN) 2010-0001, 0000152.)

Reagents: antibody dilution solution: citrate buffer (pH 5.0): 10 mM sodium citrate, 50 mM NaCl hIL-17A dilution solution: PBS (sodium phosphate buffer, pH 7.2)

Goat anti-human IgG (Fab-specific) peroxidase conjugated antibody, Sigma Cat. No. 121M4811

Protocol:

1. Procedures for Detection in Rat:

(1) In Vivo Administration

SD rats were randomly divided into two groups (an intravenous injection (IV) (dorsum of foot) group and a subcutaneous injection (SC) group), 5 rats per group;

Under sterile conditions, Hu049-18 was dissolved in a citrate buffer solution (pH 5.0) to a final concentration of 2.5 mg/mL;

Each rat was IV or SC administered with a dose of 5 mg/kg;

For the IV group, 200 uL blood samples (equivalent to 80 uL serum) were taken through the tail vein at 0 min, 5 min, 15 min, 30 min, 1 hr, 2 hr, 4 hr, 8 hr, 24 hr, 2 d, 4 d, 7 d, 10 d, 14 d, 21 d, and 28 d after administration; For the SC group, 200 uL blood samples (equivalent to 80 uL serum) were taken through the tail vein at 0 min, 30 min, 1 hr, 2 hr, 4 hr, 8 hr, 12 hr, 24 hr, 2 d, 4 d, 7 d, 10 d, 14 d, 21 d, and 28 d after administration;

Blood samples were collected and incubated for half an hour at room temperature until coagulation, and then centrifuged at 4° C., at 10000×g for 5 minutes. The supernatant was collected for immediate testing, or aliquots of the sample were stored at −80° C. Repeated freezing and thawing was avoided.

(2) Serum Samples Obtained in Step (1) were Detected by ELISA

1) Standard Curve a) Microtitration plates were directly coated with 1 µg/ml of streptavidin, and incubated at 4° C. overnight;

b) Microtitration plates were blocked with 300 μl of PBST containing 2% BSA (v/v), and thermostatically incubated at 37° C. for 1 h, and uncoated wells were blocked as controls;

c) Plates were washed with PBST three times, and all of the washing steps were performed using a Biotek (Elx 405) automatic washer;

d) 100 μl of PBS containing hIL-17A (0.2 μg/mL) were added to each well, and the plates were thermostatically incubated at 37° C. for 1 h;

e) Plates were washed with PBST three times.

f) Hu049-18 titration: 1:2 dilutions of Hu049-18 were titrated, with an initial concentration of 0.8 μg/ml. 100 μl of diluted Hu049-18 were added into each well, and the standard curve was plotted. The 96-well plate was thermostatically incubated at 37° C. for 1 h.

g) Plates were washed with PBST three times;

h) 100 μl of goat anti-human IgG (Fab-specific) peroxidase conjugated antibody (Sigma Cat. No. 121M4811) (1:5000) were added to each well, and the plates were thermostatically incubated at 37° C. for 1 h;

i) Plates were washed with PBST three times. 100 μl of TMB Substrate were added to each well, and the plates were thermostatically incubated at 37° C. for 5 min. The reaction was stopped by the addition of 100 μl M HCl to each well;

j) The OD value at a wavelength of 450 nm/630 nm was read on an ELISA microplate reader (Molecular Devices, Spectra Max).

2) Sample Test:

a) Microtitration plates were directly coated with 1 μg/ml of streptavidin, and incubated at 4° C. overnight;

b) Microtitration plates were blocked with 300 μl of PBST containing 2% BSA (v/v), and thermostatically incubated at 37° C. for 1 h, and uncoated wells were blocked as controls;

c) Plates were washed with PBST three times, and all of the washing steps were performed using a Biotek (Elx 405) automatic washer;

d) 100 μl of PBS containing hIL-17A (0.2 μg/mL) were added to each well, and the plates were thermostatically incubated at 37° C. for 1 h;

e) Plates were washed with PBST three times.

f) Serum samples titration: Before the experiment, a rat serum sample was diluted by different ratios to obtain an optimal dilution ratio at which the antibody concentration in the serum was in the middle of the standard curve. Serum samples were diluted in accordance with the optimal dilution ratio, and Hu049-18 was diluted to 25 ng/mL. 100 μl of diluted serum sample and Hu049-18 were added to each well, and the plates were thermostatically incubated at 37° C. for 1 h. Each concentration was titrated in duplicate;

g) Plates were washed with PBST three times;

h) 100 μl of goat anti-human IgG (Fab-specific) peroxidase conjugated antibody (Sigma Cat. No. 121M4811) (1:5000) were added to each well, and the plates were thermostatically incubated at 37° C. for 1 h;

i) Plates were washed with PBST three times. 100 μl of TMB Substrate were added to each well, and the plates were thermostatically incubated at 37° C. for 5 min. The reaction was stopped by the addition of 100 μl M HCl to each well;

j) The OD value at a wavelength of 450 nm/630 nm was read on an ELISA microplate reader (Molecular Devices, Spectra Max).

2. Detection Procedure for Macaques:

The in vivo detection procedure for Macaque (Macaca fascicularis) was similar to that for rats, with the following differences: the administration to cynomolgus monkey was only via intravenous injection (IV) at a dose of 1 mg/kg; 500 μL blood samples were taken through the tail vein at 0 min, 5 min, 15 min, 30 min, 1 hr, 2 hr, 4 hr, 8 hr, 24 hr, 32 hr, 3 d, 4 d, 5 d, 6 d, 9 d, 12 d, 14 d, 17 d, 21 d, 28 d, and 35 d after administration; and after centrifugation, the serum sample was divided into 3 parts (ensuring 2 parts containing 60 μL serum sample), and the samples were frozen at −80° C. for analysis.

Experimental Results:

The humanized antibody Hu049-18 obtained from Example 2 was tested according to the above method, and the results were as follows:

TABLE 11

| Animal | Administration route | T1/2 (Hu049-18) (Day) | T1/2 (Lilly mAb(hu)) (Day) |
|---|---|---|---|
| SD rat | IV (5 mg/kg) | 9.91 | 5.05 |
| | SC (5 mg/kg) | 11.5 | 5.53 |
| cynomolgus monkeys | IV (1 mg/kg) | 24.4 | |

Conclusion: These results showed that, compared to the positive control antibody of Lilly (T1/2 value of positive control antibody in cynomolgus monkeys was reported as 6.5 days (iv) and 10.3 days (sc)), the Hu049-18 antibody of the present invention had a much longer in vivo half-life under the described condition.

The invention claimed is:

1. An IL-17A binding agent comprising an antibody to IL-17A or an antigen-binding fragment thereof, wherein the antibody comprises:
   an antibody light chain variable region comprising 3 light chain complementarity determining (LCDR) regions having the amino acid sequences of SEQ ID NO: 13, SEQ ID NO: 14, and SEQ ID NO: 15, respectively; and
   an antibody heavy chain variable region comprising 3 heavy chain complementarity determining (HCDR) regions having the amino acid sequences of SEQ ID NO: 10, SEQ ID NO: 11, and SEQ ID NO: 12, respectively.

2. The IL-1A binding agent according to claim 1, wherein the antibody light chain variable region comprises a light chain FR region derived from murine κ chain, or a light chain FR region derived from a murine λ-chain.

3. The IL-17A binding agent according to claim 2, wherein the amino acid sequence of the antibody light chain variable region is shown in SEQ ID NO: 2.

4. The IL-17A binding agent according to claim 2, wherein the antibody comprises a light chain constant region derived from a murine κ chain, or a light chain constant region derived from a murine λ chain.

5. The IL-17A binding agent according to claim 1, wherein the antibody heavy chain variable region comprises a heavy chain FR region derived from murine IgG1, a heavy chain FR region derived from murine IgG2, a heavy chain FR region derived from murine IgG3, or a heavy chain FR region derived from murine IgG4.

6. The IL-17A binding agent according to claim 5, wherein the amino acid sequence of the antibody heavy chain variable region is shown in SEQ ID NO: 1.

7. The IL-17A binding agent according to claim 5, wherein the antibody comprises a heavy chain constant region derived from murine IgG1, a heavy chain constant region derived from murine IgG2, a heavy chain constant region derived from murine IgG3, or a heavy chain constant region derived from murine IgG4.

8. The IL-17A binding agent according to claim 1, wherein the antibody light chain variable region further comprises a light chain FR region derived from a human κ chain, or a light chain FR region derived from a human λ chain.

9. The IL-17A binding agent according to claim 8, wherein the light chain FR region is a human germline light chain A10 FR region having the amino acid sequence of SEQ ID NO: 4 with 0-10 amino acid substitutions.

10. The IL-17A binding agent according to claim 9, wherein the amino acid substitutions are one or more selected from the group consisting of F71Y, K49Y, Y36F and L47W.

11. The IL-17A binding agent according to claim 8, wherein the light chain FR region is a human germline light chain A10 FR region comprising the amino acid sequence of SEQ ID NO: 4.

12. The IL-17A binding agent according to claim 8, wherein the antibody comprises a light chain constant region derived from a human κ chain, or a light chain constant region derived from a human λ chain.

13. The IL-17A binding agent according to claim 1, wherein the heavy chain variable region comprises a heavy chain FR region derived from human IgG1, a heavy chain FR region derived from human IgG2, a heavy chain FR region derived from human IgG3, or a heavy chain FR region derived from human IgG4.

14. The IL-17A binding agent according to claim 13, wherein the heavy chain FR region is a variant of a heavy chain VH1-18 FR region having the amino acid sequence of SEQ ID NO: 3 with 0-10 amino acid substitutions.

15. The IL-17A binding agent according to claim 14, wherein the amino acid substitutions are one or more selected from the group consisting of A93T, T71A, M48I, V67A, M69L, T73D and S76N.

16. The IL-17A binding agent according to claim 13, wherein the heavy chain FR region is a human germline heavy chain VH1-18 FR region comprising the amino acid sequence of SEQ ID NO: 3.

17. The IL-17A binding agent according to claim 13, wherein the antibody comprises a heavy chain constant region derived from human IgG1, a heavy chain constant region derived from human IgG2, a heavy chain constant region derived from human IgG3, or a heavy chain constant region derived from human IgG4.

18. The IL-17A binding agent according to claim 1, wherein the antibody light chain variable region comprises the amino acid sequence of SEQ ID NO: 9.

19. The IL-17A binding agent according to claim 1, wherein the antibody heavy chain variable region comprises an amino acid sequence selected from the group consisting of SEQ ID NO: 5, SEQ ID NO: 6, SEQ ID NO: 7 and SEQ ID NO: 8.

20. A nucleic acid encoding the antibody according to claim 1.

21. A vector comprising the nucleic acid according to claim 20.

22. A pharmaceutical composition comprising the IL-17A binding agent according to claim 1 and a pharmaceutically acceptable excipient, diluent or carrier.

23. A method for treating a disease or disorder mediated by IL-17, the method comprising administering to a subject in need thereof a therapeutically effective amount of the pharmaceutical composition according to claim 22.

24. The method according to claim 23, wherein:
the disease is an inflammatory disease or an autoimmune disease.

25. The method according to claim 24, wherein the disease is selected from the group consisting of psoriasis, psoriatic arthritis, ankylosing spondylitis, multiple sclerosis and inflammatory arthritis.

\* \* \* \* \*

SEQUENCE LISTING

<160> NUMBER OF SEQ ID NOS: 15

<210> SEQ ID NO 1
<211> LENGTH: 123
<212> TYPE: PRT
<213> ORGANISM: mus musculus

<400> SEQUENCE: 1

His Val Gln Leu Gln Gln Ser Gly Ala Asp Leu Val Arg Pro Gly Ala
1               5                   10                  15

Ser Val Thr Leu Ser Cys Lys Ala Ser Gly Tyr Ile Phe Thr Asp Tyr
            20                  25                  30

Glu Val His Trp Val Lys Gln Thr Pro Val His Gly Leu Glu Trp Ile
        35                  40                  45

```
Gly Val Ile Asp Pro Gly Thr Gly Gly Val Ala Tyr Asn Gln Lys Phe
    50              55                  60

Glu Gly Lys Ala Thr Leu Thr Ala Asp Asp Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Thr Arg Tyr Ser Leu Phe Tyr Gly Ser Ser Pro Tyr Ala Met Asp Tyr
            100                 105                 110

Trp Gly Gln Gly Thr Ser Val Thr Val Ser Ser
            115                 120
```

<210> SEQ ID NO 2
<211> LENGTH: 106
<212> TYPE: PRT
<213> ORGANISM: mus musculus

<400> SEQUENCE: 2

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Asn Tyr Met
                20                  25                  30

His Trp Phe Gln Gln Lys Pro Gly Thr Ser Pro Lys Leu Trp Ile Tyr
            35                  40                  45

Arg Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Trp Thr
                85                  90                  95

Phe Gly Gly Gly Thr Asn Leu Glu Ile Lys
            100                 105
```

<210> SEQ ID NO 3
<211> LENGTH: 98
<212> TYPE: PRT
<213> ORGANISM: homo sapiens

<400> SEQUENCE: 3

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg
```

<210> SEQ ID NO 4
<211> LENGTH: 95
<212> TYPE: PRT
<213> ORGANISM: homo sapiens

<400> SEQUENCE: 4

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
                20                  25                  30

Leu His Trp Tyr Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 5
<211> LENGTH: 123
<212> TYPE: PRT
<213> ORGANISM: Artificial
<220> FEATURE:
<223> OTHER INFORMATION: mAb049 humanized sequence Hu049-17.VH

<400> SEQUENCE: 5

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Val His Trp Val Arg Gln Ala Pro Gly Gln Gly Leu Glu Trp Met
            35                  40                  45

Gly Val Ile Asp Pro Gly Thr Gly Gly Val Ala Tyr Asn Gln Lys Phe
        50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Arg Tyr Ser Leu Phe Tyr Gly Ser Ser Pro Tyr Ala Met Asp Tyr
            100                 105                 110

Trp Gly Gln Gly Thr Leu Val Thr Val Ser Ser
        115                 120

<210> SEQ ID NO 6
<211> LENGTH: 123
<212> TYPE: PRT
<213> ORGANISM: Artificial
<220> FEATURE:
<223> OTHER INFORMATION: mAb049 humanized sequence Hu049-18.VH

<400> SEQUENCE: 6

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Val His Trp Val Arg Gln Ala Pro Gly Gln Gly Leu Glu Trp Met
            35                  40                  45

Gly Val Ile Asp Pro Gly Thr Gly Gly Val Ala Tyr Asn Gln Lys Phe
        50                  55                  60

Glu Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
```

```
                    85                  90                  95

Thr Arg Tyr Ser Leu Phe Tyr Gly Ser Ser Pro Tyr Ala Met Asp Tyr
                100                 105                 110

Trp Gly Gln Gly Thr Leu Val Thr Val Ser Ser
            115                 120

<210> SEQ ID NO 7
<211> LENGTH: 123
<212> TYPE: PRT
<213> ORGANISM: Artificial
<220> FEATURE:
<223> OTHER INFORMATION: mAb049 humanized sequence Hu049-19.VH

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Val His Trp Val Arg Gln Ala Pro Gly Gln Gly Leu Glu Trp Ile
            35                  40                  45

Gly Val Ile Asp Pro Gly Thr Gly Gly Val Ala Tyr Asn Gln Lys Phe
        50                  55                  60

Glu Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Arg Tyr Ser Leu Phe Tyr Gly Ser Ser Pro Tyr Ala Met Asp Tyr
                100                 105                 110

Trp Gly Gln Gly Thr Leu Val Thr Val Ser Ser
            115                 120

<210> SEQ ID NO 8
<211> LENGTH: 123
<212> TYPE: PRT
<213> ORGANISM: Artificial
<220> FEATURE:
<223> OTHER INFORMATION: mAb049 humanized sequence Hu049-20.VH

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Val His Trp Val Arg Gln Ala Pro Gly Gln Gly Leu Glu Trp Ile
            35                  40                  45

Gly Val Ile Asp Pro Gly Thr Gly Gly Val Ala Tyr Asn Gln Lys Phe
        50                  55                  60

Glu Gly Arg Ala Thr Leu Thr Ala Asp Asp Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Thr Arg Tyr Ser Leu Phe Tyr Gly Ser Ser Pro Tyr Ala Met Asp Tyr
                100                 105                 110

Trp Gly Gln Gly Thr Leu Val Thr Val Ser Ser
            115                 120

<210> SEQ ID NO 9
<211> LENGTH: 107
```

```
<212> TYPE: PRT
<213> ORGANISM: Artificial
<220> FEATURE:
<223> OTHER INFORMATION: mAb049 humanized sequence Hu049VL

<400> SEQUENCE: 9

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Val Asn Tyr Met
            20                  25                  30

His Trp Phe Gln Gln Lys Pro Asp Gln Ser Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Glu Ala Glu
65                  70                  75                  80

Asp Ala Ala Thr Tyr Tyr Cys Gln Gln Arg Ser Ser Tyr Pro Trp Thr
                85                  90                  95

Phe Gly Gln Gly Thr Lys Leu Glu Ile Lys Arg
            100                 105

<210> SEQ ID NO 10
<211> LENGTH: 5
<212> TYPE: PRT
<213> ORGANISM: mus musculus

<400> SEQUENCE: 10

Asp Tyr Glu Val His
1               5

<210> SEQ ID NO 11
<211> LENGTH: 17
<212> TYPE: PRT
<213> ORGANISM: mus musculus

<400> SEQUENCE: 11

Val Ile Asp Pro Gly Thr Gly Gly Val Ala Tyr Asn Gln Lys Phe Glu
1               5                   10                  15

Gly

<210> SEQ ID NO 12
<211> LENGTH: 14
<212> TYPE: PRT
<213> ORGANISM: mus musculus

<400> SEQUENCE: 12

Tyr Ser Leu Phe Tyr Gly Ser Ser Pro Tyr Ala Met Asp Tyr
1               5                   10

<210> SEQ ID NO 13
<211> LENGTH: 10
<212> TYPE: PRT
<213> ORGANISM: mus musculus

<400> SEQUENCE: 13

Ser Ala Ser Ser Ser Val Asn Tyr Met His
1               5                   10

<210> SEQ ID NO 14
<211> LENGTH: 7
<212> TYPE: PRT
<213> ORGANISM: mus musculus
```

```
<400> SEQUENCE: 14

Arg Thr Ser Asn Leu Ala Ser
1               5

<210> SEQ ID NO 15
<211> LENGTH: 9
<212> TYPE: PRT
<213> ORGANISM: mus musculus

<400> SEQUENCE: 15

Gln Gln Arg Ser Ser Tyr Pro Trp Thr
1               5
```